(12) United States Patent
Markel

(10) Patent No.: US 12,076,365 B2
(45) Date of Patent: *Sep. 3, 2024

(54) CEACAM BASED ANTIBACTERIAL AGENTS

(71) Applicant: Gal Markel, Haifa (IL)

(72) Inventor: Gal Markel, Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/929,958

(22) Filed: Sep. 6, 2022

(65) Prior Publication Data

US 2023/0190860 A1    Jun. 22, 2023

Related U.S. Application Data

(63) Continuation of application No. 16/987,070, filed on Aug. 6, 2020, now Pat. No. 11,433,113, which is a continuation of application No. 15/896,027, filed on Feb. 13, 2018, now Pat. No. 10,765,719, which is a continuation of application No. 15/176,950, filed on Jun. 8, 2016, now Pat. No. 9,889,175, which is a continuation of application No. 13/628,541, filed on Sep. 27, 2012, now Pat. No. 9,694,046, which is a continuation of application No. 11/679,657, filed on Feb. 27, 2007, now Pat. No. 8,298,544.

(60) Provisional application No. 60/776,970, filed on Feb. 27, 2006.

(51) Int. Cl.
| | | |
|---|---|---|
| *A61K 39/00* | (2006.01) | |
| *A23L 3/34* | (2006.01) | |
| *A23L 3/3526* | (2006.01) | |
| *A23L 33/135* | (2016.01) | |
| *A23L 33/195* | (2016.01) | |
| *A61K 38/08* | (2019.01) | |
| *C07K 7/06* | (2006.01) | |

(52) U.S. Cl.
CPC ............... *A61K 38/08* (2013.01); *A23L 3/34* (2013.01); *A23L 3/3526* (2013.01); *A23L 33/135* (2016.08); *A23L 33/195* (2016.08); *C07K 7/06* (2013.01); *Y02A 50/30* (2018.01)

(58) Field of Classification Search
CPC .................................................... A61K 38/08
See application file for complete search history.

(56) References Cited

U.S. PATENT DOCUMENTS

| | | | |
|---|---|---|---|
| 6,759,045 B2 | 7/2004 | Goldenberg et al. | |
| 6,812,339 B1 | 11/2004 | Venter et al. | |
| 6,852,320 B2 | 2/2005 | Blumberg | |
| 8,298,544 B2 | 10/2012 | Markel | |
| 9,694,046 B2 | 7/2017 | Markel | |
| 9,889,175 B2 | 2/2018 | Markel | |
| 10,765,719 B2 | 9/2020 | Markel | |
| 11,433,113 B2 * | 9/2022 | Markel | ..................... A23L 3/34 |
| 2003/0190600 A1 | 10/2003 | Holmes | |
| 2003/0211477 A1 | 11/2003 | Holmes et al. | |
| 2004/0047858 A1 | 3/2004 | Blumberg et al. | |
| 2004/0209829 A1 | 10/2004 | Alpan et al. | |
| 2004/0214184 A1 | 10/2004 | Skubiiz et al. | |
| 2005/0137131 A1 | 6/2005 | Hansen et al. | |
| 2005/0267028 A1 | 12/2005 | Virji | |
| 2006/0024314 A1 | 2/2006 | Stanners et al. | |
| 2008/0242834 A1 | 10/2008 | Kieliszewski et al. | |

FOREIGN PATENT DOCUMENTS

| | | |
|---|---|---|
| WO | 9941370 | 8/1999 |
| WO | 0113937 | 3/2001 |
| WO | 0155337 | 8/2001 |
| WO | 2005099337 | 10/2005 |

OTHER PUBLICATIONS

Ritten Opinion corresponding to International Patent Application No. PCT/IB07/02870 dated Jul. 22, 2009 (8 pages).

Muchova et al., Immunoaffinity isolation of CEACAM1 on hydrazide-derivated cellulose with immobilized monoclonal antiCEA antibody, (Biomedical Chromatography vol. 15, pp. 418-422, 2001) (5 pages).

* cited by examiner

Primary Examiner — Albert M Navarro
(74) Attorney, Agent, or Firm — McAndrews, Held & Malloy, Ltd.

(57) ABSTRACT

Prophylactic and/or therapeutic antipathogen agents are provided that disrupt or prevent the formation of at least one homotypic and/or heterotypic protein-protein interaction that has at least one CEA-family protein and that is involved in the establishment and colonization of a pathogen in a suitable host.

3 Claims, No Drawings

Specification includes a Sequence Listing.

CEACAM BASED ANTIBACTERIAL AGENTS

RELATED APPLICATIONS

The present application is a continuation of U.S. patent application Ser. No. 16/987,070, filed Aug. 7, 2020, which is a continuation of U.S. patent application Ser. No. 15/896,027 filed Feb. 13, 2018, issued as U.S. Pat. No. 10,765,719 on Sep. 8, 2020, which is a continuation of U.S. patent application Ser. No. 15/176,950 filed Jun. 8, 2016, issued as U.S. Pat. No. 9,889,175 on Feb. 13, 2018, which is a continuation of U.S. patent application Ser. No. 13,628,541 filed Sep. 27, 2012, issued as U.S. Pat. No. 9,694,046 on Jul. 4, 2017, which is a continuation of U.S. patent application Ser. No. 11/679,657 filed Feb. 27, 2007, issued as U.S. Pat. No. 8,298,544 on Oct. 30, 2012, which is related to and claims priority from U.S. Provisional Patent Application Ser. No. 60/776,970, filed Feb. 27, 2006, and titled "CEACAM1 BASED ANTIMICROBIAL AGENT," the contents of which are expressly incorporated herein by reference in their entirety. Additionally, all cited references in the present applications are hereby incorporated by reference in their entirety.

BACKGROUND OF THE INVENTION

The technology of the present invention relates to the treatment, prevention, and/or decrease in the incidence of infection by a pathogenic agent. In particular, certain aspects of the present technology relate to the prevention of the colonization by a pathogen.

Examples of pathogens include microorganisms such as bacteria, viruses, protozoa, or fungi that can cause disease. Pathogens may be endogenous or exogenous. The clinical presentation of an infectious disease state reflects the interaction between the host and the microorganism. This interaction is affected by several factors including for example the host immune status and microbial virulence factors. Signs and symptoms can vary according to the site and severity of infection. The responsibility of the medical microbiology laboratory includes not only microbial detection, isolation, and identification, but also the determination of microbial susceptibility to select antimicrobial agents.

Antimicrobial agents, or antipathogen agents, generally kill, slow the growth, and/or inhibit the pathogenic action of microbes or pathogens. Included among the antimicrobial agents are antibacterial agents, antiviral agents, antifungal agents, and antiparisitic agents. In spite of the availability of effective antimicrobial drugs and vaccines, the battle against infectious diseases is far from being over. Particularly in developing countries, the emergence and spread of antimicrobial resistance is threatening to undermine the ability to treat infections and save lives. The development of new families of antimicrobials throughout the 1950s and 1960s and of modifications of these molecules through the 1970s and 1980s allowed the medical community to believe that it could always remain ahead of the pathogens. However, the pipeline of new drugs is running short and there is an impetus to develop new antimicrobials to address the global problems of drug resistance.

In addition to establishing effective public health policies regarding the proper use of antimicrobial agents, there is a general consensus that continued research and development of new antimicrobial agents is vital to keeping pace with the evolution of resistant pathogenic microbes. Over and above research regarding pharmacokinetics, pharmacodynamics, and dosage regimens, research into the identification and function of novel genes to provide the industry with new and defined targets for therapeutic intervention is paramount.

Pathogens constitute a diverse set of agents. There are correspondingly diverse ranges of mechanisms by which pathogens cause disease. The survival of most pathogens require that they colonize the host, reach an appropriate niche, avoid host defenses, replicate, and exit the infected host to spread to an uninfected one. In particular, many bacteria have unpredictable susceptibilities to antibacterial agents, and antibacterial resistance continues to cause a large number of sustained infections and deaths. Evolution of bacteria towards resistance to antimicrobial drugs, including multidrug resistance, is unavoidable because it represents a particular aspect of the general evolution of bacteria that is unstoppable. Resistance to antimicrobial drugs in bacteria can result from mutations in housekeeping structural or regulatory genes. Alternatively, resistance can result from the horizontal acquisition of foreign genetic information. The two phenomena are not mutually exclusive and can be associated in the emergence and more efficient spread of resistance.

The progression of a pathogenic bacterial infection to a disease state generally includes entry, colonization, and growth. Most infections begin with the adherence of bacteria to specific cells on the mucous membranes of the respiratory, alimentary, or genitourinary tract. Many bacteria possess surface macromolecules that bind to complementary acceptor molecules on the surfaces of certain animal cells, thus promoting specific and firm adherence. Certain of these macromolecules are polysaccharides and form a meshwork of fibers called the glycocalyx. Other proteins are specific, (e.g., M-proteins on the surface of *Streptococcus pyogenes*) which facilitate binding to the respiratory mucosal receptor. Also structures known as fimbrae may be important in the attachment process. For example, the fimbrae of *Neiseria gonorrhoeae* play a key role in the attachment of this organism to the urogenital epithelium where it causes a sexually transmitted disease. Also, it has been shown that fimbriated strains of *Escherichia coli* are much more frequent causes of urinary tract infections than strains lacking fimbrae, showing that these structures can indeed promote the capacity of bacteria to cause infection.

If a pathogen gains access to tissues by adhesion and invasion it typically multiplies by a process called colonization. Colonization typically requires that the pathogen first bind to specific tissue surface receptors and overcome any host defenses. The initial inoculum may or may not be sufficient to cause damage. A pathogen generally must grow within host tissues in order to produce disease.

The human CEA-protein family of proteins (Carcinoembryonic antigen-related) is expressed on the internal cellular lining of the gastrointestinal tract and is most likely exploited by some bacterial pathogens for colonization. The human CEA-protein family includes several distinct proteins, such as the CEACAM1 (Carcinoembryonic antigen-related cell adhesion molecule 1), CEACAM3, CEACAM5, CEACAM6 and CEACAM8. Each of these proteins has a unique expression distribution among different cells and tissues, and can interact with various target molecules, including some of the CEA protein themselves. These interactions generate a broad variety of biological functions. So far, several functions have been attributed to CEA proteins, including without limitation, the regulation of endocrine, immunologic, and cancerous processes, as well as tissue structure organization.

Various CEA proteins interact with different bacterial strains, including without limitation, some *E. coli* (an entire group of enteric bacteria), N. gonorrhea (causes gonorrhea), N. meningitides (causes severe meningitis), M. catarrhalis (causes upper respiratory infections, pneumonia and otitis media). These pathogens generally must first adhere to the appropriate internal cellular lining before causing the actual disease, in a process generally known as colonization Adding to the medical community's repertoire of available antipathogen agents, and that community's ability to fight the problem of antibacterial resistance, the present technology is directed in part to the development of new antipathogen agents derived from the human CEA-protein family of proteins or derivatives thereof. In particular, the present technology is directed to the use of human CEA-proteins, or derivatives thereof, for the prevention or retardation of a pathogenic infection, including bacterial and viral infection, and the subsequent progression to a virulent disease state.

BRIEF SUMMARY OF THE INVENTION

One object of the present invention is to provide methods, agents, and compositions for preventing and/or treating infection by a pathogen. Another object of the present invention is to provide methods, agents, and compositions for preventing colonization by a pathogen.

One or more of the preceding objects, or one or more other objects which will become plain upon consideration of the present specification, are satisfied by the invention described herein.

One aspect of the invention is a prophylactic and/or therapeutic antipathogen agent that disrupts the formation of at least one homotypic and/or heterotypic protein-protein interaction involved in the progression and/or colonization of a pathogen during infection. Another aspect of the invention, is a prophylactic and/or therapeutic agent that disrupts the formation of at least one homotypic and/or heterotypic protein-protein interaction involving at least one CEA-family protein. An agent can disrupt the formation of a protein-protein complex by preventing, interfering, slowing, reducing, or altering the equilibrium of the formation, including combinations of the forgoing.

Another aspect of the invention is a method for treating or preventing infection by a pathogen. A still further aspect of the invention is the use of an antipathogen agent for the manufacture of a medicament to treat or prevent infection by a pathogen.

In some embodiments, the antipathogen agent comprises an amino acid sequence, such as a sequence derived from a CEA-family protein sequence. A sequence is derived from another sequence when it includes some or all of the amino acids in the same order. An amino acid sequence may be a protein, peptide, polypeptide, or peptidomimetic.

DETAILED DESCRIPTION OF THE INVENTION

The present invention provides for the prevention or treatment of infection by a pathogen or combination of pathogens. As used herein a pathogen includes any endogenous or exogenous causative agent of disease. Pathogens include but are not limited to bacteria, viruses, yeast, protozoa, fungi, or any combination or derivative thereof. For example, bacterial pathogens include without limitation any E. coli species, Neisseria species, Moraxella species, Salmonella species, or any combination or derivative thereof. Exemplar viral pathogens include but are not limited to Cytomegalovirus (CMV).

The process of infection by a pathogen generally includes but is not limited to the establishment of a pathogen in or on a suitable host. The process by which a pathogen is established in or on a suitable host generally includes without limitation the association or attachment of the pathogen to a suitable host surface followed by colonization. An infection by a pathogen can occur in or on any region of the host. Infection by a pathogen can occur in or on any region of the host, including for example the skin, respiratory tract, gastrointestinal track, or any combination thereof. Infection by a pathogen can occur in or on any region of the host, including without limitation any system of the body, such as for example the skeletal, muscular, nervous, endocrine, cardiovascular, lymphatic, respiratory, digestive, urinary, reproductive, or any combination thereof. The host can be human or any lower animal, including both domestic and non-domestic animals.

One aspect of the invention is a prophylactic and/or therapeutic antipathogen agent that disrupts the formation of at least one CEA-family protein homotypic and/or heterotypic protein-protein interaction that is involved in the establishment of a pathogen in or on a suitable host and/or the progression to a disease state. As used herein a CEA-family protein includes but is not limited to CEACAM1, CEACAM3, CEACAM5, CEACAM6 and CEACAM8. An agent can disrupt the formation of a protein-protein complex by preventing, interfering, slowing, reducing, or altering the equilibrium of the formation, including combinations of the forgoing.

One aspect of the invention is a prophylactic and/or therapeutic antipathogen composition having at least one antipathogen agent that disrupts the formation of at least one homotypic and/or heterotypic protein-protein interaction that includes at least one CEA-family protein and that is involved in the establishment of a pathogen in or on a suitable host and/or the progression to a disease state. As used herein a CEA-family protein includes but is not limited to CEACAM1, CEACAM3, CEACAM5, CEACAM6 and CEACAM8.

The antipathogen agents of the present invention include but are not limited to protein, polypeptide, peptide, nucleic acid, large molecule, small molecule, derivatives and/or fragments thereof, and combinations thereof. The term "large molecule", as used herein, refers to organic or inorganic molecules either synthesized or found in nature, generally having a molecular weight greater than 1000, however the definition of large molecule is not limited by this number. The term "small molecule", as used herein, refers to organic or inorganic molecules either synthesized or found in nature, generally having a molecular weight equal to or less than 1000, however the definition of small molecule is not limited by this number.

The antipathogen agents of the present invention generally comprise at least one structural motif that prevents the formation of a protein-protein complex, or disrupts an already formed protein-protein complex, that is directly or indirectly associated with the establishment of a pathogen in or on a suitable host. As used herein, the term structural motif generally refers to any distinct grouping of chemical elements having a structure chosen based on a specified function.

The term protein includes any of various substances that comprise amino-acid residues joined by peptide bonds. The term protein includes polypeptides and peptides. The terms protein, polypeptide, peptide and "nucleic acid" include compositions of the invention that also include "analogs," or "conservative variants" and "mimetics" such as "peptidomimetics" with structures and activity that substantially correspond to the compound from which the variant was derived. For example, in some aspects of the present invention, the use of peptoids derived from one or more CEACAM protein sequences is contemplated. The synthesis and use of peptoids have previously been described in U.S. Pat. No. 5,811,387 "Peptoid mixtures" and U.S. Pat. No. 5,831,005 "Synthesis of N-substituted oligomers." These references are herein incorporated by reference.

The antipathogen agents of the present invention can be without limitation any reversible or non-reversible, competitive or non-competitive, inhibitor of the formation and/or maintenance (stability) of any homotypic and/or heterotypic protein-protein interaction that includes at least one CEA-family protein and that is involved in the establishment of a pathogen in or on a suitable host and/or the progression to a disease state.

In one embodiment of the present invention, the antipathogen agent has at least one peptide bond. These antipathogen agents include but are not limited to full-length proteins, protein structural or functional domains, smaller peptides, and peptidomimetic derivatives. For Example, these antipathogen agents can be derived from any host or pathogen protein that participates in any homotypic and/or heterotypic protein-protein interaction that is involved in the progression of a pathogen infection, including for example the adhesion, invasion, and/or establishment of a pathogen in or on a suitable host.

In one embodiment of the present invention, the antipathogen agent is a full length CEA-family protein, or a fragment derived therefrom. CEA-family proteins that can be used as antipathogen agents include but are not limited to the CEACAM1 protein represented by SEQ ID No. 1; the CEACAM3 protein represented by SEQ ID No. 2; the CEACAM5 protein represented by SEQ ID No. 3; the CEACAM6 protein represented by SEQ ID No. 4; and the CEACAM8 protein represented by SEQ ID No. 5.

In another embodiment of the present invention, the antipathogen agent comprises a fragment of a CEA-family protein. CEA-family protein fragments that can be used as antipathogen agents include but are not limited to the CEACAM1 domain 1 (Ig-like V-type N-domain) represented by SEQ ID No. 6; the CEACAM1 domain 2 (Ig-like C2-type 1) represented by SEQ ID No. 7; the CEACAM1 domain 3 (Ig-like C2-type 2) represented by SEQ ID No. 8; the CEACAM1 domain 4 (Ig-like C2-type 3) represented by SEQ ID No. 9; the CEACAM6 domain 1 (Ig-like V-type N-domain) represented by SEQ ID No. 10; the CEACAM6 domain 2 (Ig-like C2-type 1) represented by SEQ ID No. 11; the CEACAM6 domain 3 (Ig-like C2-type 2) represented by SEQ ID No. 12; CEACAM5 domain 1 (Ig-like V-type N-domain) represented by SEQ ID No. 13; the CEACAM5 domain 2 (Ig-like C2-type 1) represented by SEQ ID No. 14; the CEACAM5 domain 3 (Ig-like C2-type 2) represented by SEQ ID No. 15; the CEACAM5 domain 4 (Ig-like C2-type 3) represented by SEQ ID No. 16; the CEACAM5 domain 5 (Ig-like C2-type 4) represented by SEQ ID No. 17; the CEACAM5 domain 6 (Ig-like C2-type 5) represented by SEQ ID No. 18; and the CEACAM5 domain 7 (Ig-like C2-type 6) represented by SEQ ID No. 19.

In another embodiment of the present invention, the antipathogen agent is a full-length pathogen protein, or a fragment or domain derived therefrom. Pathogen proteins, protein domains, or protein fragments that can be used as antipathogen agents include but are not limited to those that are exposed on the bacterial cell surface and that participate in the adhesion, invasion, and/or establishment of a pathogen in or on a suitable host. For example, the *Moraxella catarrhalis* surface protein UspA1 represented by SEQ ID No. 20, or any domain, fragment or derivative thereof that binds to *Moraxella catarrhalis*, can be used as a *Moraxella catarrhalis* specific antipathogen agent. The *Neisseria meningitidis* opacity (Opa) proteins, including any domains, fragments or derivatives thereof, can also be used as *Neisseria meningitidis* specific antipathogen agents.

In another embodiment of the present invention, the antipathogen agent comprises a short linear or cyclic peptide. The peptide can be derived from any host or pathogen protein that participates in any homotypic and/or heterotypic protein-protein interaction that is involved in the progression of a pathogen infection, including for example the adhesion, invasion, and/or establishment of a pathogen in or on a suitable host. Exemplar peptides that can be used as antipathogen agents include but are not limited to the peptide NRQIV (SEQ ID No. 21) found in the CEACAM1 protein represented by SEQ ID No. 1; the peptide NRQII (SEQ ID No. 22) found in the CEACAM5 protein represented by SEQ ID No. 3; and the QNDTG peptide (SEQ ID No. 23) and the GYSWYK peptide (SEQ ID No. 24) both found in the CEACAM1 protein represented by SEQ ID No. 1, the CEACAM5 protein represented by SEQ ID No. 3, and the CEACAM6 protein represented by SEQ ID No. 4.

In another embodiment of the present invention, the antipathogen agent comprises a derivative of a peptide sequence found in the sequence of a CEACAM family protein, such as for example the CEACAM1 protein represented by SEQ ID No. 1; the CEACAM3 protein represented by SEQ ID No. 2; the CEACAM5 protein represented by SEQ ID No. 3; the CEACAM6 protein represented by SEQ ID No. 4; and the CEACAM8 protein represented by SEQ ID No. 5. In a further embodiment of the present invention, the antipathogen agent is a derivative of a peptide sequence found in the sequence of a protein expressed by a pathogen of interest and involved in the colonization of that pathogen in a host. Derivatives of any of the sequences disclosed herein can be identified, which display different binding kinetics and specificities, using standard directed evolution methods that are well known in the art. For example directed evolution methods including an iterative process of mutagenesis, expression, chromatographic selection, and amplification for the identification of new peptides having selective binding activities can be employed (Kay, B. K. et al. (2001) "Screening phage-displayed combinatorial peptide libraries."*Methods*24, 240-246. ) In certain embodiments of the present invention, the peptide NRQIV found in the CEACAM1 protein represented by SEQ ID No. 1; the peptide NRQII found in the CEACAMS protein represented by SEQ ID No. 3; and the QNDTG peptide and the GYSWYK peptide both found in the CEACAM1 protein represented by SEQ ID No. 1, the CEACAMS protein represented by SEQ ID No. 3, and the CEACAM6 protein represented by SEQ ID No. 4 can be used as the basic scaffold in a directed evolution experiment designed to identify different peptides having a different binding specificities and/or kinetics. For example, the Ph.D™ Phage Display Cloning System from New England Biolabs can be used to create CEACAM derived peptide libraries on the surface of bacteriophage M13 as coat protein fusions, creating a physical linkage between each displayed peptide and its encoding DNA sequence, and which allows rapid partitioning based on binding affinity to a given target molecule (such as a pathogen protein) by an in vitro selection process called panning (Whaley, S. R. et al. (2000) *Nature*, 405, 665-668. )

In another embodiment of the present invention, the antipathogen agent comprises a small molecule compound. The term "small molecule" includes any small molecule, either synthesized or found in nature, such as an organic molecule, inorganic molecule, or a synthetic molecule, such as those generated by combinatorial chemistry methodologies. These small molecules can be synthesized using a variety of procedures and methodologies, which are well described in the scientific and patent literature, e.g., Organic Syntheses Collective Volumes, Gilman et al. (Eds) John Wiley & Sons, Inc., N.Y.; Venuti (1989) *Pharm Res.* 6:867-873. This reference is herein incorporated by reference. Synthesis of small molecules, as with all other procedures associated with this invention, can be practiced in conjunction with any method or protocol known in the art. For example, preparation and screening of combinatorial chemical libraries are well known, see, e.g., U.S. Pat. Nos. 6,096,496; 6,075,166; 6,054,047; 6,004,617; 5,985,356; 5,980,839; 5,917,185; 5,767,238. These references are herein incorporated by reference.

In a further embodiment of the present invention, the antipathogen agent comprises derived from a random library of compounds by selection or screening. The compounds include but are not limited to compounds having at least one peptide bond, nucleic acids, large molecules, small molecules, or any combinations or derivatives thereof.

In another embodiment of the present invention, the antipathogen agent comprises a multimer antipathogen agent comprising at least two or more antipathogen agents, according to the present invention, linked together. The antipathogen agents, linked together to form the multimer antipathogen agent, can be identical or different, and can include but are not limited to any combination of protein, nucleic acid, large molecule, small molecule, or derivatives thereof.

In certain embodiments of the present invention, the antipathogen is formulated in a suitable dosage form. Dosage forms include but are not limited to pills, dragees, tablets, capsules, solutions, liquids, slurries, suspensions, suppositories, emulsions, troches, transdermal patches, oral powders, oral mists, and oral strips. Any suitable material can be used to make the dosage form, including for example starch, sucrose, maltose, maltodextrin, and saccharin. Any suitable route of administration can be employed including for example oral, inhaled, intravenous, intramuscular, intra-arterial, intramedullary, intrathecal, intraventricular, subcutaneous, intraperitoneal, transdermal, intradermal, intranasal, jejunal, topical, sublingual, and/or rectal.

In still other embodiments, antipathogen agents according to the present invention can be added to solid foodstuffs, liquid foodstuffs, powdered foodstuffs, medicinal solutions, non-medicinal solutions, medicinal aerosols, non-medicinal aerosols, non-animate solid surfaces, or any combination or derivative thereof.

In other embodiments, antipathogen agents according to the present invention can be added to a nutraceutical composition. As used herein, a nutraceutical is any foodstuff that provides health benefits, including without limitation a fortified food or dietary supplement. A nutraceutical includes but is not limited to any substance that can be considered a food or part of a food and provides medical or health benefits, including the prevention and treatment of disease.

In one particular embodiment of the present invention, commercial milk remedies for children are supplemented with the antipathogen agents of the present invention, including for example those that are specific for those pathogens causing childhood diseases such as diarrhea, bacterial meningitis and bacterial upper respiratory infections. Examples of pathogens include without limitation pathogenic *E. coli* that cause, for example, diarrhea. Pathogens also include but are not limited to *Neisseria* species, including for example *N. gonorrhoeae* and *N. meningitidis*, *Moraxella Catarrhalis* and *Haemophilus* species, including for example, *H. influenza*.

In yet another embodiment, probiotics can be genetically engineered to produce one or more of the antipathogen agents of the present invention. Probiotics include without limitation live bacterial preparations having clinical health effects when presented to a host. Probiotics can be derived or engineered from bacteria that normally inhabit the gastrointestinal system of the host, or bacteria typically associated with dairy fermentation and fermented dairy products. For example, the probiotic can be derived from, or engineered from bacteria of the genera Lactobacillus, Bifidobacterium, Escherichia, Enterococcus, or *Bacillus*. The probiotic can be presented for example as a culture concentrate, or inoculated into a milk-based food. The probiotic can also be formulated as concentrated and dried cells packaged as dietary additives.

A still further aspect of the present invention regards increasing the uptake of lipids in the human gastrointestinal (GI) tract. This aspect of the invention can be achieved by contacting the GI track with the CEACAM1 protein and/or derivatives of the CEACAM1 protein. For example, the CEACAM1 protein and/or derivatives of the CEACAM1 protein can be added in soluble or non-soluble form to any dietary source of lipids. As used herein, in connection with this aspect of the present invention, a lipid includes without limitation a relatively water-insoluble or nonpolar compound such as micelles, fatty acids, fatty-acid derived phospholipids, sphingolipids, glycolipids and terpenoids, such as retinoids and steroids.

SEQUENCE LISTING

```
Sequence total quantity: 24
SEQ ID NO: 1            moltype = AA   length = 526
FEATURE                 Location/Qualifiers
REGION                  1..526
                        note = MISC_FEATURE - NCBI accession number P13688
source                  1..526
                        mol_type = protein
                        organism = Homo sapiens
SEQUENCE: 1
MGHLSAPLHR VRVPWQGLLL TASLLTFWNP PTTAQLTTES MPFNVAEGKE VLLLVHNLPQ    60
QLFGYSWYKG ERVDGNRQIV GYAIGTQQAT PGPANSGRET IYPNASLLIQ NVTQNDTGFY   120
TLQVIKSDLV NEEATGQFHV YPELPKPSIS SNNSNPVEDK DAVAFTCEPE TQDTTYLWWI   180
NNQSLPVSPR LQLSNGNRTL TLLSVTRNDT GPYECEIQNP VSANRSDPVT LNVTYGPDTP   240
```

```
TISPSDTYYR PGANLSLSCY AASNPPAQYS WLINGTFQQS TQELFIPNIT VNNSGSYTCH    300
ANNSVTGCNR TTVKTIIVTE LSPVVAKPQI KASKTTVTGD KDSVNLTCST NDTGISIRWF    360
FKNQSLPSSE RMKLSQGNTT LSINPVKRED AGTYWCEVFN PISKNQSDPI MLNVNYNALP    420
QENGLSPGAI AGIVIGVVAL VALIAVALAC FLHFGKTGRA SDQRDLTEHK PSVSNHTQDH    480
SNDPPNKMNE VTYSTLNFEA QQPTQPTSAS PSLTATEIIY SEVKKQ                   526

SEQ ID NO: 2           moltype = AA   length = 292
FEATURE                Location/Qualifiers
REGION                 1..292
                       note = MISC_FEATURE - NCBI accession number AAQ88451
source                 1..292
                       mol_type = protein
                       organism = Homo sapiens
SEQUENCE: 2
MGPPSACPHR ECIPWQGLLL TASLLTFWNA PTTAWLFIAS APFEVAEGEN VHLSVVYLPE    60
NLYSYGWYKG KTVEPNQLIA AYVIDTHVRT PGPAYSGRET ISPSGDLHFQ NVTLEDTGYY    120
NLQVTYRNSQ IEQASHHLRV YESVAQPSIQ ASSTTVTEKG SVVLTCHTNN TGTSFQWIFN    180
NQRLQVTKRM KLSWFNHVLT IDPIRQEDAG EYQCEVSNPV SSNRSDPLKL TVKYDNTLGI    240
LIGVLVGSLL VAALVCFLLL RKTGRASDQS DFREQQPPAS TPGHGPSDSS IS            292

SEQ ID NO: 3           moltype = AA   length = 702
FEATURE                Location/Qualifiers
REGION                 1..702
                       note = MISC_FEATURE - NCBI accession number P06731
source                 1..702
                       mol_type = protein
                       organism = Homo sapiens
SEQUENCE: 3
MESPSAPPHR WCIPWQRLLL TASLLTFWNP PTTAKLTIES TPFNVAEGKE VLLLVHNLPQ    60
HLFGYSWYKG ERVDGNRQII GYVIGTQQAT PGPAYSGREI IYPNASLLIQ NIIQNDTGFY    120
TLHVIKSDLV NEEATGQFRV YPELPKPSIS SNNSKPVEDK DAVAFTCEPE TQDATYLWWV    180
NNQSLPVSPR LQLSNGNRTL TLFNVTRNDT ASYKCETQNP VSARRSDSVI LNVLYGPDAP    240
TISPLNTSYR SGENLNLSCH AASNPPAQYS WFVNGTFQQS TQELFIPNIT VNNSGSYTCQ    300
AHNSDTGLNR TTVTTITVYA EPPKPFITSN NSNPVEDEDA VALTCEPEIQ NTTYLWWVNN    360
QSLPVSPRLQ LSNDNRTLTL LSVTRNDVGP YECGIQNELS VDHSDPVILN VLYGPDDPTI    420
SPSYTYYRPG VNLSLSCHAA SNPPAQYSWL IDGNIQQHTQ ELFISNITEK NSGLYTCQAN    480
NSASGHSRTT VKTITVSAEL PKPSISSNNS KPVEDKDAVA FTCEPEAQNT TYLWWVNGQS    540
LPVSPRLQLS NGNRTLTLFN VTRNDARAYV CGIQNSVSAN RSDPVTLDVL YGPDTPIISP    600
PDSSYLSGAN LNLSCHSASN PSPQYSWRIN GIPQQHTQVL FIAKITPNNN GTYACFVSNL    660
ATGRNNSIVK SITVSASGTS PGLSAGATVG IMIGVLVGVA LI                      702

SEQ ID NO: 4           moltype = AA   length = 344
FEATURE                Location/Qualifiers
REGION                 1..344
                       note = MISC_FEATURE - NCBI accession number P40199
source                 1..344
                       mol_type = protein
                       organism = Homo sapiens
SEQUENCE: 4
MGPPSAPPCR LHVPWKEVLL TASLLTFWNP PTTAKLTIES TPFNVAEGKE VLLLAHNLPQ    60
NRIGYSWYKG ERVDGNSLIV GYVIGTQQAT PGPAYSGREI IYPNASLLIQ NVTQNDTGFY    120
TLQVIKSDLV NEEATGQFHV YPELPKPSIS SNNSNPVEDK DAVAFTCEPE VQNTTYLWWV    180
NGQSLPVSPR LQLSNGNMTL TLLSVKRNDA GSYECEIQNP ASNRSDPVT LNVLYGPDVP    240
TISPSKANYR PGENLNLSCH AASNPPAQYS WFINGTFQQS TQELFIPNIT VNNSGSYMCQ    300
AHNSATGLNR TTVTMITVSG SAPVLSAVAT VGITIGVLAR VALI                    344

SEQ ID NO: 5           moltype = AA   length = 349
FEATURE                Location/Qualifiers
REGION                 1..349
                       note = MISC_FEATURE - NCBI accession number P31997
source                 1..349
                       mol_type = protein
                       organism = Homo sapiens
SEQUENCE: 5
MGPISAPSCR WRIPWQGLLL TASLFTFWNP PTTAQLTIEA VPSNAAEGKE VLLLVHNLPQ    60
DPRGYNWYKG ETVDANRRII GYVISNQQIT PGPAYSNRET IYPNASLLMR NVTRNDTGSY    120
TLQVIKLNLM SEEVTGQFSV HPETPKPSIS SNNSNPVEDK DAVAFTCEPE TQNTTYLWWV    180
NGQSLPVSPR LQLSNGNRTL TLLSVTRNDV GPYECEIQNP ASANFPVT LNVLYGPDAP    240
TISPSDTYYH AGVNLNLSCH AASNPPSQYS WSVNGTFQQY TQKLFIPNIT TKNSGSYACH    300
TTNSATGRNR TTVRMITVSD ALVQGSSPGL SARATVSIMI GVLARVALI              349

SEQ ID NO: 6           moltype = AA   length = 98
FEATURE                Location/Qualifiers
REGION                 1..98
                       note = MISC_FEATURE - CEACAM1 domain #1 (Ig-like V-type
                       N-domain)
source                 1..98
                       mol_type = protein
                       organism = Homo sapiens
```

```
SEQUENCE: 6
QLTTESMPFN VAEGKEVLLL VHNLPQERVD GNRQIVGYAI GTQQATPGPA NSGRETIYPN    60
ASLLIQNVTQ NDTGFYTLQV IKSDLVNEEA TGQFHVYP                           98

SEQ ID NO: 7            moltype = AA   length = 91
FEATURE                 Location/Qualifiers
REGION                  1..91
                        note = MISC_FEATURE - CEACAM1 domain #2 (Ig-like C2-type 1)
source                  1..91
                        mol_type = protein
                        organism = Homo sapiens
SEQUENCE: 7
PKPSISSNNS NPVEDKDAVA FTCEPETQDT TYLWWINNQS LPVSPRLQLS NGNRTLTLLS    60
VTRNDTGPYE CEIQNPVSAN RSDPVTLNVT Y                                  91

SEQ ID NO: 8            moltype = AA   length = 81
FEATURE                 Location/Qualifiers
REGION                  1..81
                        note = MISC_FEATURE - CEACAM1 domain #3 (Ig-like C2-type 2)
source                  1..81
                        mol_type = protein
                        organism = Homo sapiens
SEQUENCE: 8
PDTPTISPSD TYYRPGANLS LSCYAASNPP AQYSWLINGT FQQSTQELFI PNITVNNSGS    60
YTCHANNSVT GCNRTTVKTI I                                             81

SEQ ID NO: 9            moltype = AA   length = 91
FEATURE                 Location/Qualifiers
REGION                  1..91
                        note = MISC_FEATURE - CEACAM1 domain #4 (Ig-like C2-type 3)
source                  1..91
                        mol_type = protein
                        organism = Homo sapiens
SEQUENCE: 9
PVVAKPQIKA SKTTVTGDKD SVNLTCSTND TGISIRWFFK NQSLPSSERM KLSQGNTTLS    60
INPVKREDAG TYWCEVFNPI SKNQSDPIML N                                  91

SEQ ID NO: 10           moltype = AA   length = 108
FEATURE                 Location/Qualifiers
REGION                  1..108
                        note = MISC_FEATURE - CEACAM6 domain #1 (Ig-like V-type
                        N-domain)
source                  1..108
                        mol_type = protein
                        organism = Homo sapiens
SEQUENCE: 10
KLTIESTPFN VAEGKEVLLL AHNLPQNRIG YSWYKGERVD GNSLIVGYVI GTQQATPGPA    60
YSGRETIYPN ASLLIQNVTQ NDTGFYTLQV IKSDLVNEEA TGQFHVYP                108

SEQ ID NO: 11           moltype = AA   length = 88
FEATURE                 Location/Qualifiers
REGION                  1..88
                        note = MISC_FEATURE - CEACAM6 domain #2 (Ig-like C2-type 1)
source                  1..88
                        mol_type = protein
                        organism = Homo sapiens
SEQUENCE: 11
PKPSISSNNS NPVEDKDAVA FTCEPEVQNT TYLWWVNGQS LPVSPRLQLS NGNMTLTLLS    60
VKRNDAGSYE CEIQNPASAN RSDPVTLN                                      88

SEQ ID NO: 12           moltype = AA   length = 78
FEATURE                 Location/Qualifiers
REGION                  1..78
                        note = MISC_FEATURE - CEACAM6 domain #3 (Ig-like C2-type 2)
source                  1..78
                        mol_type = protein
                        organism = Homo sapiens
SEQUENCE: 12
PDVPTISPSK ANYRPGENLN LSCHAASNPP AQYSWFINGT FQQSTQELFI PNITVNNSGS    60
YMCQAHNSAT GLNRTTVT                                                 78

SEQ ID NO: 13           moltype = AA   length = 110
FEATURE                 Location/Qualifiers
REGION                  1..110
                        note = MISC_FEATURE - CEACAM5 domain #1 (Ig-like V-type
                        N-domain)
source                  1..110
                        mol_type = protein
                        organism = Homo sapiens
```

```
SEQUENCE: 13
KLTIESTPFN VAEGKEVLLL VHNLPQHLFG YSWYKGERVD GNRQIIGYVI GTQQATPGPA    60
YSGREIIYPN ASLLIQNIIQ NDTGFYTLHV IKSDLVNEEA TGQFRVYPEL              110

SEQ ID NO: 14           moltype = AA  length = 92
FEATURE                 Location/Qualifiers
REGION                  1..92
                        note = MISC_FEATURE - CEACAM5 domain #2 (Ig-like C2-type 1)
source                  1..92
                        mol_type = protein
                        organism = Homo sapiens
SEQUENCE: 14
KPSISSNNSK PVEDKDAVAF TCEPETQDAT YLWWVNNQSL PVSPRLQLSN GNRTLTLFNV    60
TRNDTASYKC ETQNPVSARR SDSVILNVLY GP                                 92

SEQ ID NO: 15           moltype = AA  length = 85
FEATURE                 Location/Qualifiers
REGION                  1..85
                        note = MISC_FEATURE - CEACAM5 domain #3 (Ig-like C2-type 2)
source                  1..85
                        mol_type = protein
                        organism = Homo sapiens
SEQUENCE: 15
DAPTISPLNT SYRSGENLNL SCHAASNPPA QYSWFVNGTF QQSTQELFIP NITVNNSGSY    60
TCQAHNSDTG LNRTTVTTIT VYAEP                                         85

SEQ ID NO: 16           moltype = AA  length = 92
FEATURE                 Location/Qualifiers
REGION                  1..92
                        note = MISC_FEATURE - CEACAM5 domain #4 (Ig-like C2-type 3)
source                  1..92
                        mol_type = protein
                        organism = Homo sapiens
SEQUENCE: 16
KPFITSNNSN PVEDEDAVAL TCEPEIQNTT YLWWVNNQSL PVSPRLQLSN DNRTLTLLSV    60
TRNDVGPYEC GIQNELSVDH SDPVILNVLY GP                                 92

SEQ ID NO: 17           moltype = AA  length = 83
FEATURE                 Location/Qualifiers
REGION                  1..83
                        note = MISC_FEATURE - CEACAM5 domain #5 (Ig-like C2-type 4)
source                  1..83
                        mol_type = protein
                        organism = Homo sapiens
SEQUENCE: 17
DDPTISPSYT YYRPGVNLSL SCHAASNPPA QYSWLIDGNI QQHTQELFIS NITEKNSGLY    60
TCQANNSASG HSRTTVKTIT VSA                                           83

SEQ ID NO: 18           moltype = AA  length = 92
FEATURE                 Location/Qualifiers
REGION                  1..92
                        note = MISC_FEATURE - CEACAM5 domain #6 (Ig-like C2-type 5)
source                  1..92
                        mol_type = protein
                        organism = Homo sapiens
SEQUENCE: 18
KPSISSNNSK PVEDKDAVAF TCEPEAQNTT YLWWVNGQSL PVSPRLQLSN GNRTLTLFNV    60
TRNDARAYVC GIQNSVSANR SDPVTLDVLY GP                                 92

SEQ ID NO: 19           moltype = AA  length = 84
FEATURE                 Location/Qualifiers
REGION                  1..84
                        note = MISC_FEATURE - CEACAM5 domain #7 (Ig-like C2-type 6)
source                  1..84
                        mol_type = protein
                        organism = Homo sapiens
SEQUENCE: 19
DTPIISPPDS SYLSGANLNL SCHSASNPSP QYSWRINGIP QQHTQVLFIA KITPNNNGTY    60
ACFVSNLATG RNNSIVKSIT VSAS                                          84

SEQ ID NO: 20           moltype = AA  length = 873
FEATURE                 Location/Qualifiers
REGION                  1..873
                        note = MISC_FEATURE - NCBI accession number AAF40122
source                  1..873
                        mol_type = protein
                        organism = Moraxella catarrhalis
SEQUENCE: 20
MNKIYKVKKN AAGHLVACSE FAKGHTKKAV LGSLLIVGIL GMATTASAQQ TIARQGKGMH    60
```

```
SIIGGGNDNE ANGDYSTVSG GDYNEAKGDS STIGGGYYNE ANGDSSTIGG GFYNEAKGES  120
STIGGGDNNS ATGMYSTIGG GDNNSATGRY STIAGGWLNQ ATGHSSTVAG GWLNQATNEN  180
STVGGGRFNQ ATGRNSTVAG GYKNKATGVD STIAGGRNNQ ANGIGSFAAG IDNQANANNT  240
VALGNKNIIK GKDSVAIGSN NTVETGKENV FILGSNTKDA HSNSVLLGNE TTGKAATTVE  300
NAKVGGLSLT GFVGASKANT NNGTVSVGKQ GKERQIVNVG AGQIRADSTD AVNGSQLHAL  360
ATAVDAEFRT LTQTQNALIE QGEAINQELE GLADYTNAQD EKILKNQTDI TANKTAIEQN  420
FNRTVTNGFE IEKNKAGIAK NQADIQTLEN DVGKELLNLS GRLLDQKADI DNNINNIYEL  480
AQQQDQHSSD IKTLKNNVEE GLLDLSGRLI DQKADLTKDI KALENNVEEG LLDLSGRLID  540
QKADIAKNQA DIQDLAAYNE LQDQYAQKQT EAIDALNKAS SANTDRIATA ELGIAENKKD  600
AQIAKAQANE NKDGIAKNQA DIANNIKNIY ELAQQQDQHS SDIKTLAKVS AANTDRIAKN  660
KAEADASFET LTKNQNTLIE QGEALVEQNK AINQELEGFA AHADVQDKQI LQNQADITAN  720
KTAIEQNINR TVANGFEIEK NKAGIATNKQ ELILQHDRLN RINETNNRQD QKIDQLGYAL  780
KEQGQHFNNR ISAVERQTAG GIANAIAIAT LPSPSRAGEH HVLFGSGYHN GQAAVSLGAA  840
GLSDTGKSTY KIGLSWSDAG GLSGGVGGSY RWK                              873

SEQ ID NO: 21           moltype = AA  length = 5
FEATURE                 Location/Qualifiers
source                  1..5
                        mol_type = protein
                        organism = Homo sapiens
SEQUENCE: 21
NRQIV                                                               5

SEQ ID NO: 22           moltype = AA  length = 5
FEATURE                 Location/Qualifiers
source                  1..5
                        mol_type = protein
                        organism = Homo sapiens
SEQUENCE: 22
NRQII                                                               5

SEQ ID NO: 23           moltype = AA  length = 5
FEATURE                 Location/Qualifiers
source                  1..5
                        mol_type = protein
                        organism = Homo sapiens
SEQUENCE: 23
QNDTG                                                               5

SEQ ID NO: 24           moltype = AA  length = 6
FEATURE                 Location/Qualifiers
source                  1..6
                        mol_type = protein
                        organism = Homo sapiens
SEQUENCE: 24
GYSWYK                                                              6
```

What is claimed is:

1. A multimer therapeutic agent consisting of two or more different isolated peptides selected from the group consisting of SEQ ID No. 21-SEQ ID No. 24, wherein the therapeutic agent is an antipathogen agent.

2. A multimer therapeutic agent consisting of the isolated peptides NRQIV (SEQ ID No. 21), NRQII (SEQ ID No. 22), QNDTG (SEQ ID No. 23), and GYSWYK (SEQ ID. No. 24), wherein the therapeutic agent is an antipathogen agent.

3. A multimer therapeutic agent consisting of the isolated peptides NRQII (SEQ ID No. 22), QNDTG (SEQ ID No. 23), and GYSWYK (SEQ ID. No. 24), wherein the therapeutic agent is an antipathogen agent.

* * * * *